United States Patent
Hlavinka et al.

(10) Patent No.: US 7,829,867 B2
(45) Date of Patent: Nov. 9, 2010

(54) APPARATUS FOR PHOTO REDUCTION OF CONTAMINANTS IN BLOOD AND BLOOD PRODUCTS WITH CALIBRATION MEANS

(75) Inventors: Dennis J. Hlavinka, Arvada, CO (US); Terrence M. Cussen, Englewood, CO (US); Daniel T. McGinnis, Lakewood, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 317 days.

(21) Appl. No.: 12/032,963

(22) Filed: Feb. 18, 2008

(65) Prior Publication Data

US 2009/0010806 A1    Jan. 8, 2009

Related U.S. Application Data

(60) Provisional application No. 60/947,592, filed on Jul. 2, 2007.

(51) Int. Cl.
  *A61L 2/08*    (2006.01)
  *G21K 5/02*    (2006.01)
(52) U.S. Cl. .............................. 250/455.11; 250/453.11; 422/1; 422/22
(58) Field of Classification Search ..................... 435/2, 435/448, 173.1, 183, 184, 236, 244; 422/23, 422/24, 28, 29, 44, 186, 1, 40, 292, 307; 250/455.11, 453.11, 434.11, 493.1, 494.1, 250/495.1, 503.1, 504 R, 428, 429, 431, 432 R, 250/433, 436, 437, 336.1, 338.1, 339.06, 250/339.09; 702/19, 22, 28, 40
  See application file for complete search history.

(56) References Cited

U.S. PATENT DOCUMENTS 4,551,628 A    11/1985    Grossman (Continued)

FOREIGN PATENT DOCUMENTS

WO    WO00/74731    12/2000

(Continued)

OTHER PUBLICATIONS

Prodouz et al, "Use of Laser-UV for Inactivation of Virus in Blood Products", *Blood*, Aug. 1987, 70(2):589-592.

(Continued)

*Primary Examiner*—Jack I Berman
*Assistant Examiner*—Nicole Ippolito Rausch
(74) *Attorney, Agent, or Firm*—John R. Merkling; Enda M. O'Connor; Laura B. Arciniegas

(57) ABSTRACT

An apparatus for irradiating blood or blood products, preferably with ultra violet or visible light, to reduce contaminants in the blood or blood products. A removable radiometer having light integrating chambers detects the light intensity, allowing the radiation characteristics of the apparatus to be calibrated. A control circuit uses the measurements to control the delivery of an effective dose of illumination to blood or blood products in a bag or container. One or more light integrating optical chambers in the radiometer allow a single light sensor to sense light across an entire field. Thermistors in the irradiating apparatus or the radiometer or both sense the temperature of photo sensors. The control circuit compensates for temperature-dependant variations in the output of the photo sensors.

17 Claims, 7 Drawing Sheets

U.S. PATENT DOCUMENTS

| | | | |
|---|---|---|---|
| 4,868,383 | A | 9/1989 | Kurtz et al. |
| 4,884,896 | A * | 12/1989 | Conway .................... 374/9 |
| 4,952,812 | A | 8/1990 | Miripol et al. |
| 5,103,385 | A | 4/1992 | Federico et al. |
| 5,146,341 | A | 9/1992 | Erck et al. |
| 5,215,370 | A | 6/1993 | Kaplan |
| 5,386,267 | A | 1/1995 | Jones |
| 5,442,533 | A | 8/1995 | Kaplan |
| 5,511,106 | A * | 4/1996 | Doebert et al. ............ 378/146 |
| 5,527,704 | A | 6/1996 | Wolf, Jr. et al. |
| 5,548,120 | A | 8/1996 | Parker et al. |
| 5,565,958 | A | 10/1996 | Kaplan |
| 5,658,722 | A | 8/1997 | Margolis-Nunno et al. |
| 5,762,867 | A | 6/1998 | D'Silva |
| 5,868,695 | A | 2/1999 | Wolf, Jr. et al. |
| 5,889,684 | A * | 3/1999 | Ben-David et al. ......... 700/282 |
| 6,258,577 | B1 | 7/2001 | Goodrich, Jr. et al. |
| 6,268,120 | B1 | 7/2001 | Platz et al. |
| 6,277,337 | B1 | 8/2001 | Goodrich, Jr. et al. |
| 6,437,861 | B1 | 8/2002 | Kuta |
| 6,810,161 | B2 | 10/2004 | Flower et al. |
| 6,843,961 | B2 | 1/2005 | Hlavinka et al. |
| 7,068,361 | B2 | 6/2006 | Cimino et al. |
| 2003/0165398 | A1 * | 9/2003 | Waldo et al. ................. 422/22 |
| 2004/0191125 | A1 * | 9/2004 | Kellogg et al. ............... 422/72 |
| 2005/0269521 | A1 * | 12/2005 | Zagrobelny ................ 250/435 |
| 2006/0257877 | A1 * | 11/2006 | Anderle et al. ................ 435/6 |

FOREIGN PATENT DOCUMENTS

| | | |
|---|---|---|
| WO | WO03/063915 | 8/2003 |
| WO | WO2006/021314 | 3/2006 |

OTHER PUBLICATIONS

International Search Report for PCT/US2008/054219, mailed Jun. 5, 2008.

* cited by examiner

APPARATUS FOR PHOTO REDUCTION OF CONTAMINANTS IN BLOOD AND BLOOD PRODUCTS WITH CALIBRATION MEANS

This application describes an apparatus for irradiating blood or blood products, preferably with ultra violet or visible light, to reduce contaminants in the blood or blood products. A removable radiometer having light integrating chambers detects the light intensity, allowing the radiation characteristics of the apparatus to be calibrated. A control circuit uses the measurements to control the delivery of an effective dose of illumination to blood or blood products in a bag or container. One or more light integrating chambers in the radiometer allow a single light sensor to sense light across an entire field.

BACKGROUND

Contamination of whole blood or blood products with infectious microorganisms such as HIV, hepatitis and other viruses and bacteria present a serious health hazard for those who must receive transfusions of whole blood or administration of various blood products or blood components such as platelets, red cells, blood plasma, Factor VIII, plasminogen, fibronectin, anti-thrombin III, cryoprecipitate, human plasma protein fraction, albumin, immune serum globulin, prothrombin complex plasma growth hormones, and other components isolated from blood. Blood screening procedures may miss pathogenic contaminants, and sterilization procedures which do not damage cellular blood components but effectively inactivate all infectious viruses and other microorganisms have not heretofore been available.

In some circumstances, certain blood components may themselves be harmful to the desired blood product. For example, white blood cells, which are part of the donor's immune system, may cause an adverse reaction in the recipient of a red blood cell product. Many white cells are separated by centrifugation from the desired red blood cells, but some usually remain mixed with the red blood cells. The undesired white blood cells may be considered a "contaminant" or "pathogen" with respect to the desired relatively pure red blood cell product. The white blood cells may be inactivated in the same manner as an infectious virus or microorganism.

The use of pathogen inactivating agents include certain photo sensitizers, or compounds which absorb light of defined wavelengths and transfer the absorbed energy to an energy acceptor, have been proposed for inactivation of microorganisms found in blood products or fluids containing blood products. Such photo sensitizers may be added to the fluid containing blood or blood products and irradiated.

The photo sensitizers which may be used in this invention include any photo sensitizers known to the art to be useful for inactivating microorganisms. A "photo sensitizer" is defined as any compound which absorbs radiation at one or more defined wavelengths and subsequently utilizes the absorbed energy to carry out a chemical process. Examples of photo sensitizers which may be used for the reduction of pathogens in blood or blood products include porphyrins, psoralens, dyes such as neutral red, methylene blue, acridine, toluidines, flavine (acriflavine hydrochloride) and phenothiazine derivatives, coumarins, quinolones, quinones, and anthroquinones.

A number of systems and methods for irradiating pathogens in a fluid with light either with or without the addition of a photo sensitizer are known in the art. For example, U.S. Pat. No. 5,762,867 is directed toward a system for activating a photoactive agent present in a body fluid with light emitting diodes (LEDs).

U.S. Pat. No. 5,527,704 is directed toward an apparatus containing LEDs used to activate a fluid containing methylene blue.

U.S. Pat. No. 5,868,695 discloses using LEDs having a red color and emitting light at a wavelength of 690 nm in combination with benzoporphrin derivative photo sensitizers to inactivate red blood cells. As taught in this patent, at a wavelength of 690 nm, red blood cells are essentially transparent to radiation, and as such, the benzoporphorin derivatives absorb radiation at this wavelength to become activated. Also disclosed in this patent is the use of LEDs having a blue color and emitting light at a peak wavelength of 425 mn to inactivate platelets.

U.S. Pat. No. 5,658,722 discloses irradiating platelets using UVA1 light having an emission peak near 365 nm. This patent teaches that damage to platelets is caused by short UVA<345 nm, and unlike the present invention, calls for removing UVA wavelengths below 345 nm.

Use of light which is variably pulsed at a wavelength of 308 nm without the addition of a photo sensitizer to inactivate virus in a washed platelet product is taught in an article by Prodouz et al. (Use of Laser-UV for Inactivation of Virus in Blood Products; Kristina Prodouz, Joseph Fratantoni, Elizabeth Boone and Robert Bonner; Blood, Vol 70, No. 2). This article does not teach or suggest the addition of a photo sensitizer in combination with light to kill viruses.

U.S. Pat. No. 6,843,961 is directed toward the reduction of pathogens which may be present in blood or blood products using light having peak wavelengths in combination with an endogenous photo sensitizer.

Whether or not a photo sensitizer is used, it is important that the dosage of radiation delivered to the blood or blood component be accurately controlled. Proper calibration of the irradiation apparatus is, therefore, necessary.

SUMMARY OF THE INVENTION

The present invention provides an apparatus for irradiating a fluid containing blood products and pathogens, including a radiometer for accurate calibration of delivered radiation. The apparatus comprises treatment chamber having at least one radiation emitting source emitting radiation; a support platform for holding the fluid containing blood cells or blood components to be irradiated; a control unit for controlling the radiation emitting source; and a removable radiometer in electrical communication with the control unit, the radiometer comprising a first optical chamber having a aperture for receiving at least some of the radiation and a photo sensor responsive to the received radiation in the optical chamber. The optical chamber may comprise an elongated cavity or cylinder, with an aperture shaped as a slot extending parallel to a long dimension of the optical chamber. This aperture might be covered by or filled with a light transmitting material such as quartz glass. An inner surface of the optical chamber may be "optically rough", producing a diffuse or lambertion reflection. The inner surface may be coated with or made from TEFLON™ or other suitable material.

The photo sensor may be coupled to a thermistor through a heat sink. The output of the photo sensor may be correlated to a detected temperature, whereby a more accurate measurement of illumination may be obtained.

In a further aspect of the invention related to an illuminator, a photo sensor in the illuminator responds to radiation emitted by the radiation source and communicates a signal to the control unit. A thermistor detects temperature changes and communicates a signal to the control unit, which correlates the photo sensor signal with respect to the temperature signal.

It has been found that the photo sensor signal is a function both of received light and of temperature, and that actual illumination can be more accurately controlled if the illuminator senses the temperature of the photodiode. Further, the illuminator may comprise a plurality of light sources and a plurality of photo diodes, at least some of the photodiodes being mounted in a heat sink. The thermistor may be coupled to the heat sink.

In another aspect of the invention the radiometer may further comprise a first integrating chamber coupled to the first optical chamber by an opening, which may be a second slot. The second slot may be generally perpendicular to the first slot with respect to an axis of symmetry of the first optical chamber. Where there are two or more coupled optical chambers, the sensor is preferably in the last chamber, for example, in the first integrating chamber.

In a further aspect of the invention, the sensor is recessed away from an inner surface of the optical chamber. This may eliminate the use of a baffle. The recess may be "apodized", that is, optically sharp corners or discontinuities may be removed. The sensor may be mounted diametrically across the first optical chamber from the second slot.

The apparatus may also have a second radiation emitting source emitting radiation, wherein the radiometer is mounted between the first radiation emitting source and the second radiation emitting source. The radiometer may further comprise a second optical chamber having a third aperture for receiving at least some of said radiation from the second radiation source and a second photo sensor responsive to the radiation received in the third optical chamber.

In another embodiment of the invention, the apparatus comprises a first integrating chamber coupled to the first optical chamber by an opening and a second integrating chamber coupled to the second optical chamber by another opening. The optical chambers may be parallel, elongated cylinders having substantially parallel longitudinal axes of symmetry and the apertures and the openings may be slots, the slots being substantially parallel to the axes of symmetry.

These and other features of the invention will be apparent from the following detailed description, taken with reference to the accompanying drawings.

DETAILED DESCRIPTION

Figure 1:
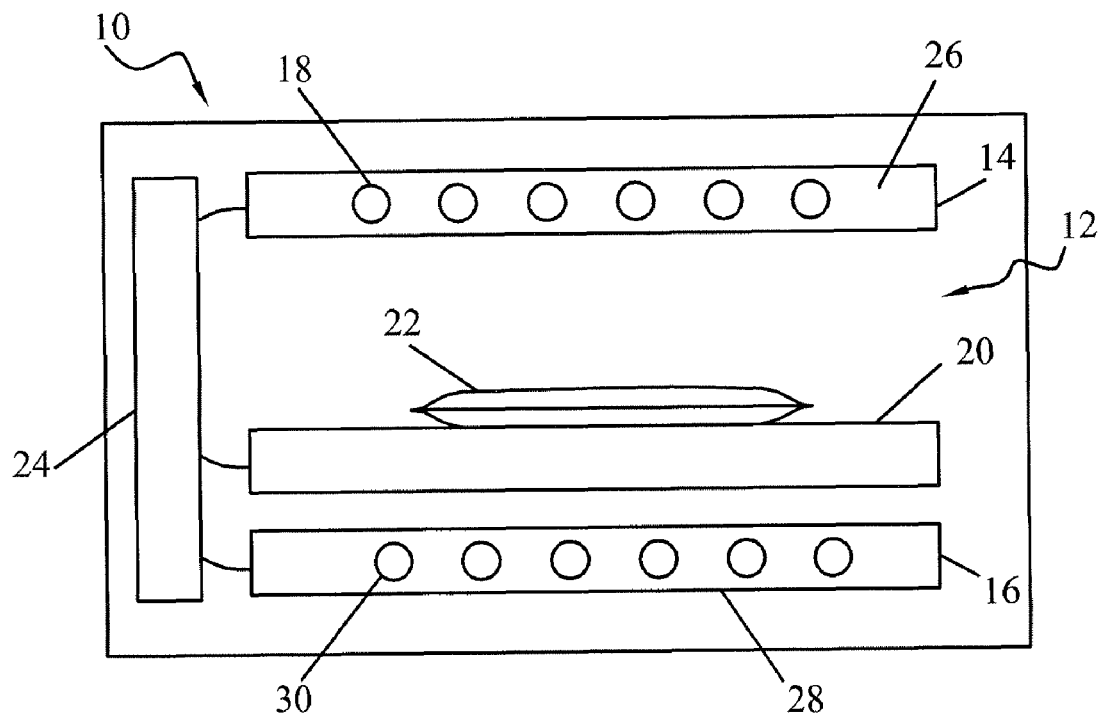
FIG. 1 is a cross-sectional view of a treatment chamber in an illuminator which may be used in the present invention.

The term "blood product" as used herein includes all blood constituents or blood components and therapeutic protein compositions containing proteins derived from blood as described above. Fluids containing biologically active proteins other than those derived from blood may also be treated by the methods and devices of this invention.

Photo sensitizers may include compounds which preferentially adsorb to nucleic acids, thus focusing their photodynamic effect upon microorganisms and viruses with little or no effect upon accompanying cells or proteins. Other types of photo sensitizers are also useful in this invention, such as those using singlet oxygen-dependent mechanisms.

Most preferred are endogenous photo sensitizers. The term "endogenous" means naturally found in a human or mammalian body, either as a result of synthesis by the body or by ingestion as an essential foodstuff (e.g. vitamins) or formation of metabolites and/or byproducts in vivo. Examples of such endogenous photo sensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photo sensitizers include synthetically derived analogs and homologs of endogenous photo sensitizers which may have or lack lower (1-5) alkyl or halogen substituents of the photo sensitizers from which they are derived, and which preserve the function and substantial non-toxicity thereof. When endogenous photo sensitizers are used, particularly when such photo sensitizers are not inherently toxic or do not yield toxic photoproducts after photo radiation, no removal or purification step is required after decontamination, and a treated product can be directly returned to a patient's body or administered to a patient in need of its therapeutic effect without any further required processing. Using endogenous photo sensitizers to inactivate pathogens in a blood product are described in U.S. Pat. Nos. 6,843,961, 6,258,577 and 6,277,337, herein incorporated by reference in their entirety to the amount not inconsistent. In U.S. Pat. No. 6,843,961, the photo sensitizer used in the examples is 7,8-dimethyl-10-ribityl isoalloxazine (riboflavin). Non-endogenous photo sensitizers based on endogenous structures, such as those described in U.S. Pat. No. 6,268,120, may also be used in the present invention, and is incorporated by reference herein. Upon exposure of the photo sensitizer to light of a particular wavelength, the photo sensitizer will absorb the light energy, causing photolysis of the photo sensitizer and any nucleic acid bound to the photo sensitizer.

Microorganisms or pathogens which may be eradicated or inactivated using pathogen inactivation agents or photo sensitizers include, but are not limited to, viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include Φ X174, Φ 6, λ, R17, $T_4$, and $T_2$. Exemplary bacteria include but are not limited to *P. aeruginosa, S. aureus, S. epidermis, L. monocytogenes, E. coli, K. pneumonia* and *S. marcescens*.

The fluid to be pathogen inactivated has the photo sensitizer added thereto, and the resulting fluid mixture may be exposed to photo radiation of the appropriate peak wavelength and amount to activate the photo sensitizer, but less than that which would cause significant non-specific damage to the biological components or substantially interfere with biological activity of other proteins present in the fluid. Accurate control of the amount of radiation delivered to the fluid is, therefore, important.

The term peak wavelength as defined herein means that the light is emitted in a narrow range centered around a wavelength having a particular peak intensity. Visible light for pathogen reduction may be centered around a wavelength of approximately 470 nm, and having a maximum intensity at approximately 470 nm. In another embodiment, the light may be centered around a narrow range of UV light at an approximate wavelength of 302 nm, and having a maximum intensity at approximately 302 nm. The term light source or radiation source as defined herein means an emitter of radiant energy, and may include energy in the visible and/or ultraviolet range, as further described below.

The photo sensitizer may be added directly to the fluid to be pathogen inactivated, or may be flowed into the photo-permeable container separately from the fluid being treated, or may be added to the fluid prior to placing the fluid in the photo-permeable treatment container. The photo sensitizer may also be added to the photo-permeable container either before or after sterilization of the treatment container.

The fluid containing the photo sensitizer may also be flowed into and through a photo-permeable container for irradiation, using a flow through type system. Alternatively, the fluid to be treated may be placed in a photo-permeable container which is agitated and exposed to photo radiation for a time sufficient to substantially inactivate the microorganisms, in a batch-wise type system.

The term "container" refers to a closed or open space, which may be made of rigid or flexible material, e.g., may be a bag or box or trough. The container may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima® and/or Spectra™ apheresis systems of Gambro, Inc., (f/k/a Cobe Laboratories, Inc., Lakewood, Colo., USA), have been used to exemplify another embodiment involving a batch-wise treatment of the fluid.

The term "photo-permeable" means the material of the treatment container is adequately transparent to photo radiation of the proper wavelength for activating the photo sensitizer. In a flow-through system, the container has a depth (dimension measured in the direction of the radiation from the photo radiation source) sufficient to allow photo radiation to adequately penetrate the container to contact photo sensitizer molecules at all distances from the light source and ensure inactivation of pathogens in the fluid to be decontaminated, and a length (dimension in the direction of fluid flow) sufficient to ensure a sufficient exposure time of the fluid to the photo radiation. The materials for making such containers, as well as the depths and lengths of the containers may be easily determined by those skilled in the art, and together with the flow rate of fluid through the container, the intensity of the photo radiation and the absorptivities of the fluid components, e.g., plasma, platelets, red blood cells, will determine the amount of time the fluid should be exposed to photo radiation. The container used may be any container known in the art for holding fluid to be irradiated, including, but not limited to blood bags, cuvettes and tubing. One example, not meant to be limiting which may be used as the container is an Extended Life Platelet (ELP) bag available from Gambro BCT, Inc. Another example of a suitable container is the Sangewald bag (available from Sangewald Verpackungen GmbH & Co. KG).

After treatment, the blood or blood product may be stored for later delivery to a patient, concentrated, infused directly into a patient or otherwise processed for its ultimate use.

Figure 2:
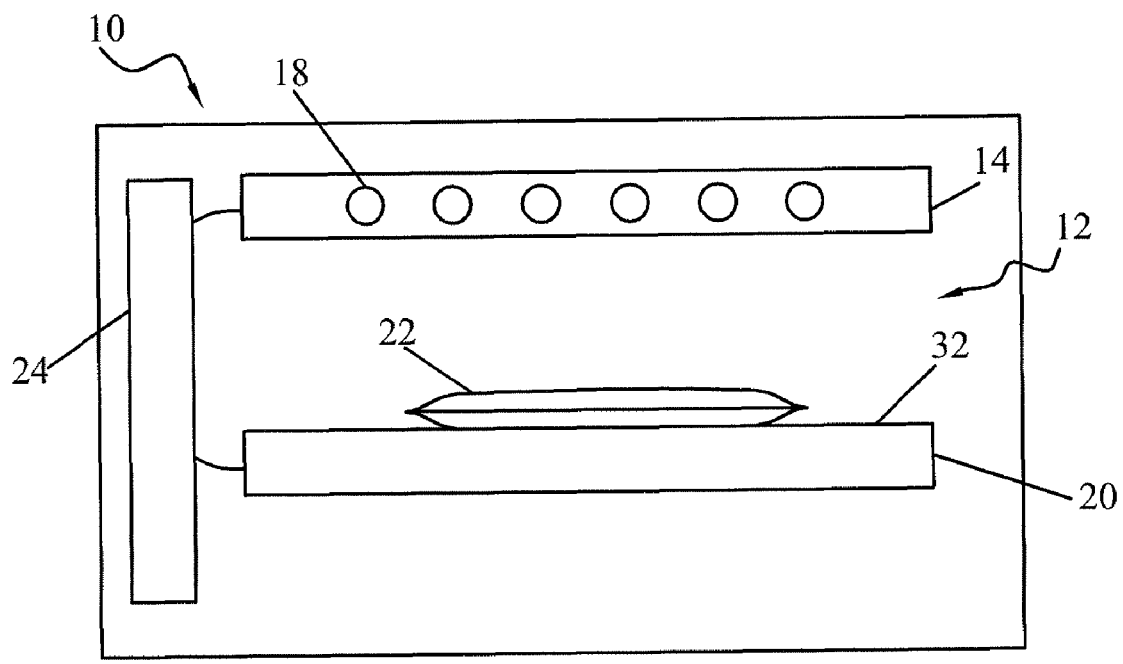
FIG. 2 is a cross-sectional view of another treatment chamber.

FIG. 1 shows, in a cross-sectional view, the inside of a radiation or treatment chamber of one type of apparatus that may be used in the present invention. The treatment chamber shown in FIG. 1 may be used in batch-wise systems, however, it should be noted that similar elements may also be used in flow-through systems. It should be noted that throughout the description of the invention, like elements have been given like numerals. The apparatus 10, used for inactivating a fluid which may contain pathogens, consists of an radiation chamber 12 having at least one source of radiation 14. In one preferred embodiment (FIG. 1), the radiation chamber may contain a second source of radiation 16. A single light source, as shown in FIG. 2, may also be used. Each radiation source 14 and 16 respectively, is depicted as including a plurality of discrete radiation-emitting elements 18, 30. The radiation chamber 12 further consists of a support platform 20 for supporting a fluid container 22 containing the fluid to be irradiated, and a control unit 24.

As introduced above, two sources of radiation are shown within radiation chamber 12. Radiation source 14 may be located along the top portion of the radiation chamber 12 above the container 22, which holds or contains the fluid to be irradiated, while radiation source 16 may be located along the bottom portion of the radiation chamber 12 below the container 22. Although not shown, radiation sources may also be located along some or all of the sides of the radiation chamber 12 perpendicular to the container 22. The radiation chamber 12 may alternatively contain a single radiation source at any location within the radiation chamber 12 and still comply with the spirit and scope of the present invention.

The upper radiation source 14 includes an upper support substrate 36 supporting a plurality of discrete radiation emitting elements or discrete light sources (see discrete source 18 as one example) mounted thereon. As further depicted in FIG. 1, the lower radiation source 16 includes a lower support substrate 28 which also supports a plurality of discrete radiation emitting elements or discrete light sources (see discrete source 30 as another example). Lower support substrate 28 preferably runs parallel to support platform 20. The support substrates 36, 28 may be substantially flat as shown, or may be in an arcuate shape, or may be in a shape other than arcuate, without departing from the spirit and scope of the invention.

The support substrate may or may not have reflective surfaces. In a further alternative configuration, the reflective surface may not contain any light sources. Such a reflective surface containing no light sources (not shown) may be located within the radiation chamber 12 on a side opposite from the radiation source. The support platform 20 may have a reflective surface 32. This reflective surface 32 on support platform 20 may be in place of, or may be in addition to another reflective surface within the radiation chamber. There may also be no reflective surfaces at all within the radiation chamber.

In any of these reflective surface embodiments, the reflective surface may be coated with a highly reflective material which serves to reflect the radiation emitted from the lights back and forth throughout the treatment chamber until the radiation is preferably completely absorbed by the fluid being irradiated. The highly reflective nature of the reflective surface reflects the emitted light back at the fluid-filled bag or container 22 with minimum reduction in the light intensity.

In FIG. 1, support platform 20 is positioned within the radiation chamber 12. The support platform 20 may be located substantially in the center of the radiation chamber (as shown in FIG. 1), or may be located closer to either the top portion or the bottom portion of the treatment chamber. The support platform 20 supports the container 22 containing the fluid to be irradiated. Additionally or alternatively, the platform 20 may be made of a photo-permeable material to enable radiation emitted by the lights to be transmitted through the platform and penetrate the fluid contained within the container 22. The platform may also be a wire or other similar mesh-like material to allow maximum light transmissivity therethrough.

The support platform 20 is preferably capable of movement in multiple directions within the radiation chamber 12. One type of agitation system used might be similar to the Helmer flatbed agitation system available from Helmer Corp. (Noblesville, Ind., USA). This type of agitator provides to and fro motion. Other types of agitators may also be used to provide a range of motion to the fluid contained within the container 22. For example, the support platform might be oriented in a vertical direction with the light substrates 36 and 28 also oriented in a vertical direction. The support platform 20 may alternatively rotate in multiple possible directions within the radiation chamber in varying degrees from between 0° to 360°. Support platform 20 may also oscillate back and forth, or side to side along the same plane. As a further alternative, one or more of the light sources may also move in a coordinated manner with the movement of the support platform. Such oscillation or rotation would enable the majority of the photo sensitizer and fluid contained within the container 22 to be exposed to the light emitted from each of the discrete radiation sources (e.g. discrete sources 18 and 30), by continually replacing the exposed fluid at the light-fluid interface with fluid from other parts of the bag not yet exposed to the light. Such mixing continually brings to the surface new fluid to be exposed to light. The movement of both the support platform 20 and/or the radiation sources 14 and 16 may be controlled by control unit 24. The control unit 24 may also control the rate of light emission.

In a preferred embodiment each discrete light source 18 and 30 emits a peak wavelength of light to irradiate the fluid contained in bag 22. The peak wavelength of light emitted by each discrete light source is selected to provide irradiation of a sufficient intensity to activate both the photo sensitizer in a pathogen inactivation process as well as to provide sufficient penetration of light into the particular fluid being irradiated, without causing significant damage to the blood or blood components being irradiated. The preferred photo sensitizer is riboflavin. To irradiate a fluid containing red blood cells and riboflavin, it is preferred that each discrete light source 18 and 30 be selected to emit light at a peak wavelength of about 302 nm. Alternatively, 470 nm light might be used. The 470 nm of light is close to the optimal wavelength of light to both photolyse riboflavin, and also to enable significant penetration of the fluid containing red blood cells by the light.

If desired, the light sources 18 and 30 may be light emitting diodes and might be pulsed. Pulsing the light may be advantageous because the intensity of light produced by the light sources may be increased dramatically if the lights are allowed to be turned off and rested between light pulses. Pulsing the light at a high intensity also allows for greater depth of light penetration into the fluid being irradiated, thus allowing a thicker layer of fluid to be irradiated with each light pulse.

Figure 3:
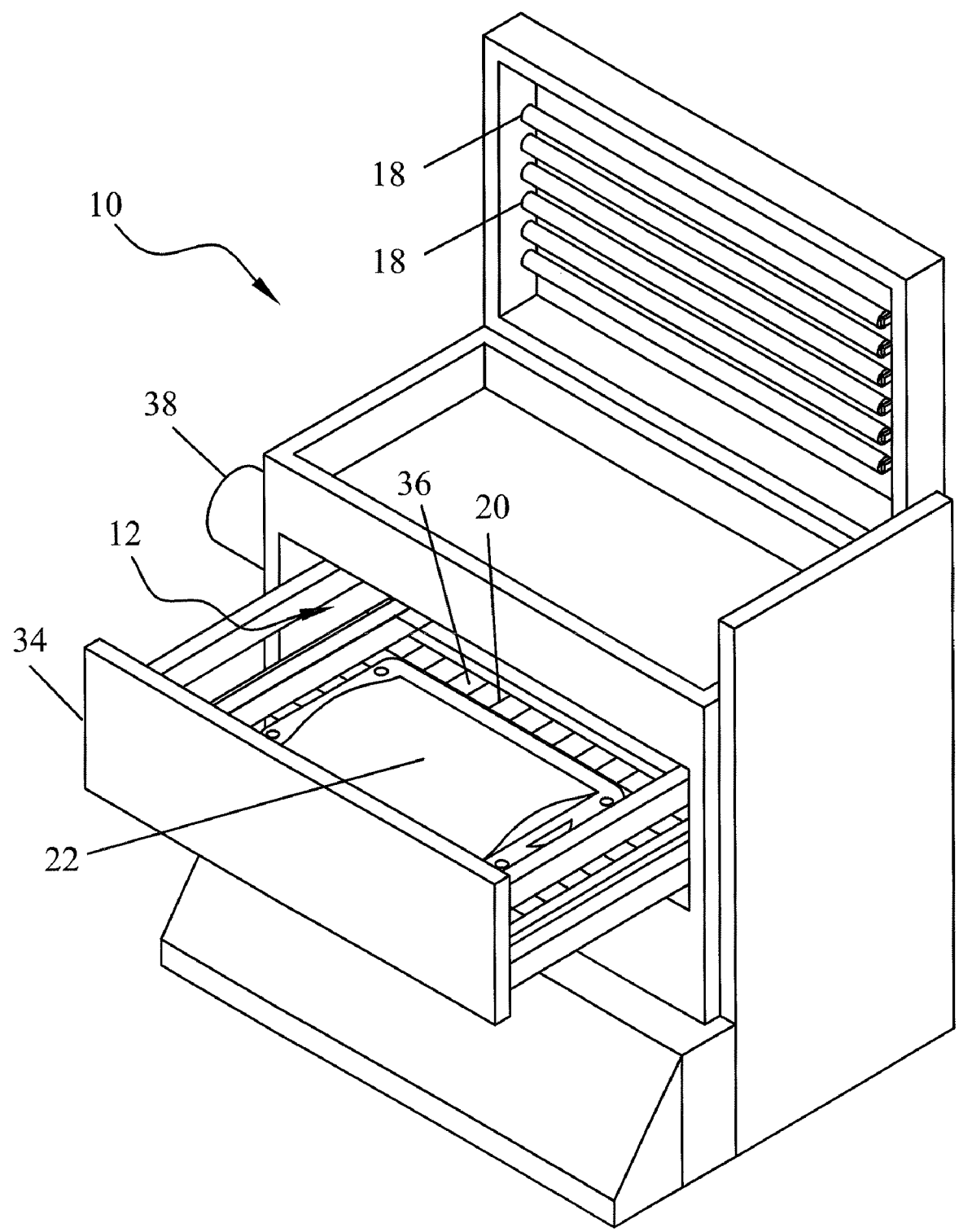
FIG. 3 is a perspective view of an irradiation apparatus or illuminator containing a treatment chamber.

The light sources 18 as shown in FIG. 3, may be fluorescent or incandescent tubes, which stretch the length of the irradiation chamber, or may be a single light source which extends the length and width of the entire chamber (not shown). LEDs may also be used in this embodiment. As shown in FIG. 3, the support platform 20 may be located within and/or forming part of a drawer 34. The support platform 20 may contain gaps 36 or holes or spaces within the platform 20 to allow radiation to penetrate through the gaps directly into the container 22 containing fluid to be irradiated.

A cooling system may also optionally be included. Air cooling using at least one fan 38 may be preferred but it is understood that other well-known systems can also be used. Although not shown in FIG. 3, the method may also include the use of temperature sensors and other cooling mechanisms where necessary to keep the temperature below temperatures at which desired proteins and blood components in the fluid being irradiated are damaged. Preferably, the temperature is kept between about 0° C. and about 45° C., more preferably between about 4° C. and about 37° C., and most preferably about 28° C.

Figure 4:
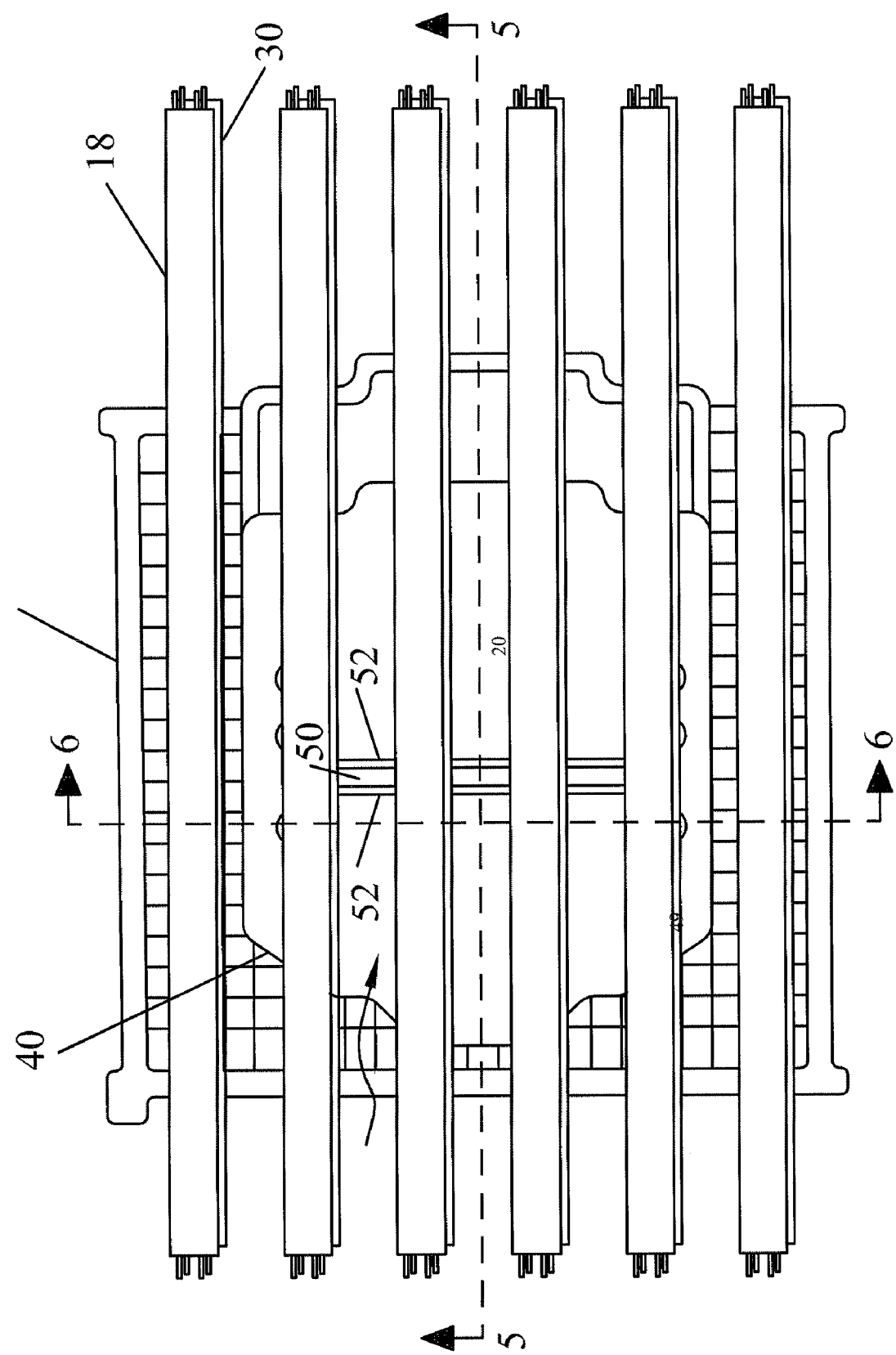
FIG. 4 is a top plan view of elements of a treatment chamber, with a calibration radiometer.
Figure 5:
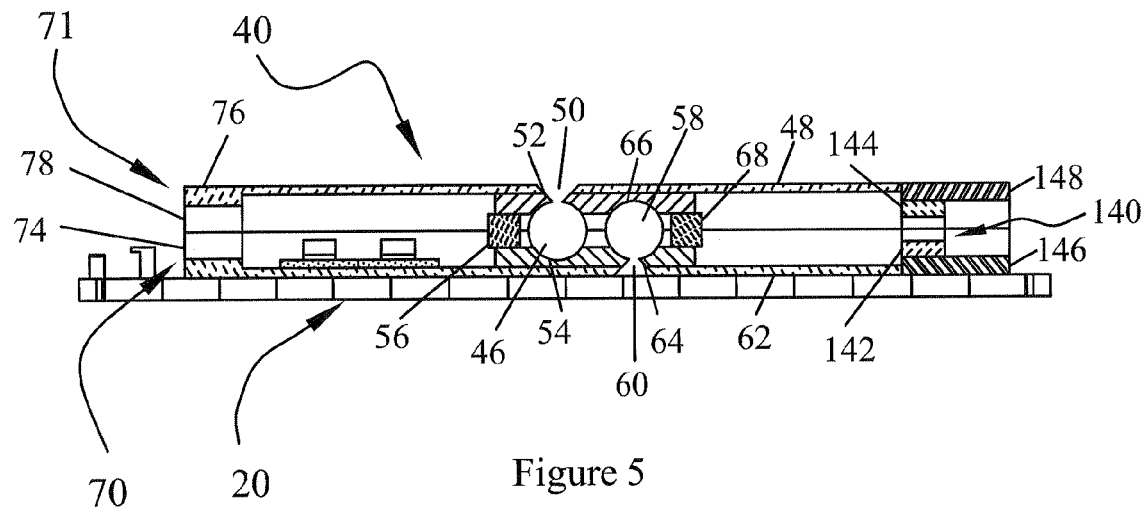
FIG. 5 is a cross-sectional plan view of the elements of FIG. 4, taken along line 5-5 of FIG. 4.
Figure 6:
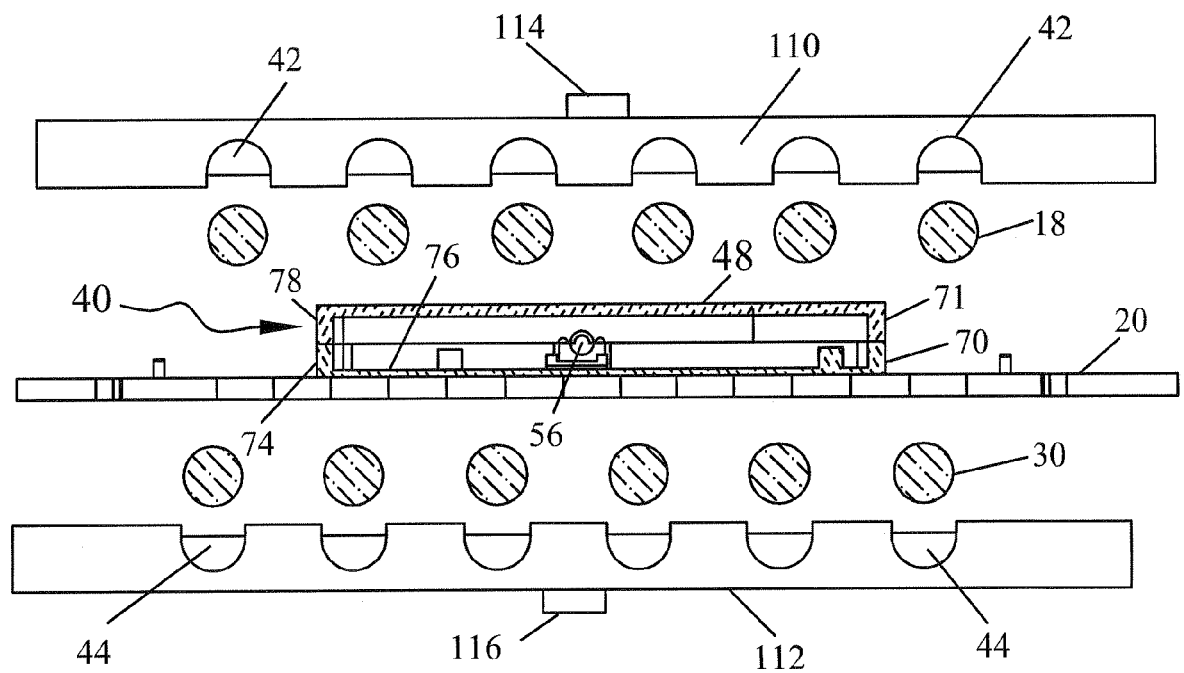
FIG. 6 is a cross-sectional plan view of the elements of FIG. 4, taken along line 6-6 of FIG. 4.

The present invention includes a removable radiometer 40 that has the general shape of a blood bag 22. When placed on the support platform 20 and electrically connected to the controller 24, the radiometer 40 detects the intensity of incident light, preferably ultraviolet light, thereby allowing for calibration of the apparatus 10. Once calibrated, the controller 24 will be able to adjust exposure time and light intensity to deliver a desired dose of radiation to a blood bag and its contents. As shown in FIGS. 4, 5 and 6, the support platform or platen 20 carries the radiometer 40 backwards and forwards parallel to the ultraviolet florescent light sources 18. The stroke distance allows the sensing apparatus (described below) of the radiometer to "view" the light sources 18, 30. Each of the light sources 18, 30 has an associated photo sensor 42, 44 (FIG. 6) in electrical communication with the controller 24. During calibration, the controller 24 correlates the signals from the photo sensors 42, 44 to the output of the radiometer 40. When the radiometer 40 has been removed and replaced with a blood bag, the controller 24 will control the dose of radiation received by the blood bag based on the calibrated signals received from the photo sensors 42, 44.

The photo sensors 42, 44 may be mounted in heat sinks 110, 112. Thermistors 114, 116 detect the temperature of the photo sensors 42, 44 as represented by the temperature of the heat sinks 110, 112 and communicate a signal to the controller 24. It has been found that the output signals of the photo sensors 42, 44 are dependant not only on the incident light received by a photo sensor, but also on temperature, that is, increased temperature will elevate the output of the photo sensor for the same intensity of incident light. With signals from both the thermistor and the photo sensor, the controller can more accurately control the dose of radiation received by the blood bag and its contents.

The radiometer 40 comprises at least one elongated, cylindrical optical chamber. If light is supplied solely from one side, for example, from the upper lamps 18, a first or upward-opening optical chamber 46 may be provided, oriented generally perpendicularly to the tubes 18 and to a reciprocating movement of the platen 20. An upper surface 48 of the radiometer 40 has a slot 50 parallel to the elongated axis of the optical chamber 46, which allows light from the lamps 18 to enter the optical chamber. The edges 52 of the slot 50 are preferably chamfered to allow light from most of the length of the lamps to be received in the chamber 46. Reciprocating movement of the platen 20 brings additional lengths of the lamps at each end into the view of the chamber 46. Thus, the radiation received through the slot 50 approximates the radiation received by a blood sample and sample bag along a line at the position of the slot. Because the chamber "averages" the non-uniform light field emitted by the lamps 18, the exposure on this line can be used to calculate the total exposure dose received by the sample.

An inner surface 54 of the optical chamber 46 is optically rough and coated with or made from a suitable substance such as TEFLON™ material, allowing light received in the chamber to reflect within the chamber in such a way that the light field becomes averaged at any point within the chamber. A single photo sensor 56, mounted in the inner surface 54 perpendicularly from the slot 50, can sense an intensity representative of the radiation being received along the entire length of the slot. Preferably, the photo sensor 50 is recessed away from the inner surface 54, to reduce the likelihood of a beam of light or radiation from the lamps 18 falling directly on the photo sensor 56 without at least one reflection from the inner surface 54 of the chamber. Multiple photo sensors may also be used.

In an embodiment having a lower bank of lamps 30, the radiometer 40 preferably has a second downward-opening optical chamber 58. The second optical chamber 58 is oriented parallel to the first optical chamber 46 and also comprises a slot 60 in a lower surface 62 of the radiometer 40, the slot 60 being parallel to the elongated axis of the second optical chamber 58, but oriented in an opposite direction from the slot 50 in the first chamber 46, which allows light from the lower lamps 30 to enter the second optical chamber 58. The edges 64 of the slot 60 are preferably chamfered, as explained above, and reciprocating movement of the platen 20 brings additional lengths of the lower lamps at each end into the view of the lower chamber 58. An inner surface 66 of the optical chamber 58 is optically rough and coated with or made from a suitable substance such as TEFLON™ material. As explained above, a single photo sensor 68, mounted in the inner surface 66 perpendicularly from the slot 60, is recessed away from the inner surface 66. Although a single photo sensor in each optical chamber is preferred, a plurality of photo sensors could also be used.

Figure 7:
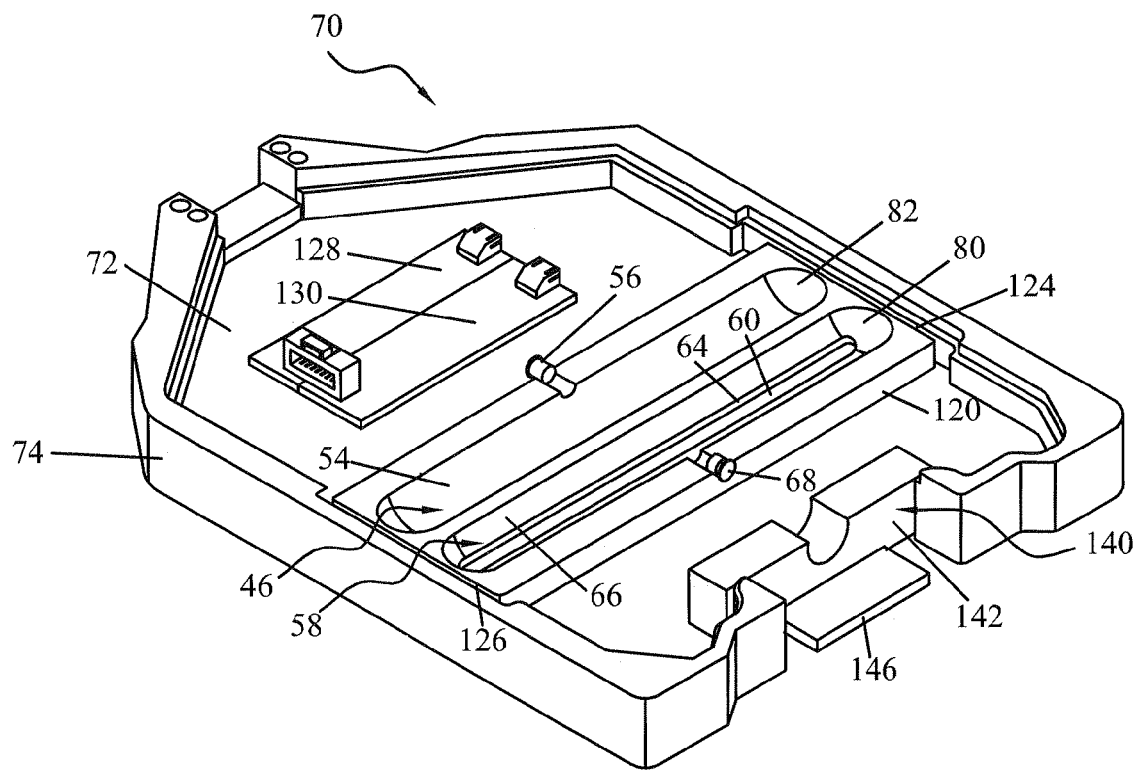
FIG. 7 is a perspective view of a radiometer.
Figure 8:
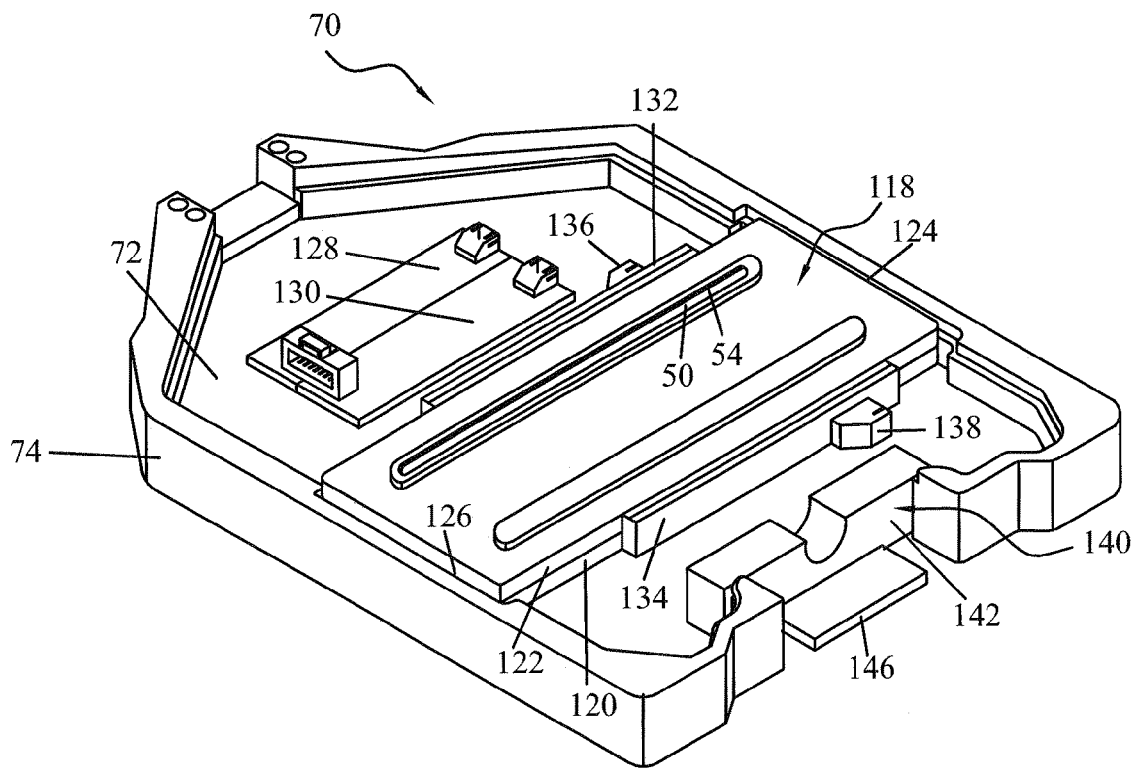
FIG. 8 is a further perspective view of the radiometer of FIG. 7.

The radiometer 40 comprises an upper shell 71 and a lower shell 70. The lower shell 70, as shown in FIG. 7 and FIG. 8, has a bottom surface 72 and a peripheral wall 74, the peripheral wall having the general shape of a blood bag of a type that might be used in the illuminator 10. The upper shell 71 has a top surface 48 and a mating peripheral wall 78 (see FIG. 5 and FIG. 6), adapted to fit against the peripheral wall 74 of the lower shell 70. As explained above, first and second optical chambers 46, 58 are provided. These chambers 46, 58 comprise mating half-cylinders 80, 82 in the lower shell 70 and upper half-cylinders in the upper shell 71. In the embodiment shown in FIG. 7 and FIG. 8, the chambers 46, 58 are within an inner box 118 having a lower portion 120 and an upper portion 122. Heat sinks 132, 134 cover the photo diodes 56, 68 on the outside of the box 118. Thermistors 136, 138, in thermal contact with the heat sinks 132, 134 respond to the temperature of the heat sinks, which is also representative of the temperature of the photo diodes 56, 68. The output of the photodiodes is a function not only of the incident illumination, but also of the temperature of the photodiode. Thus, as the temperature of the photodiode increases, the output current of the photodiode will also rise, even if the illuminating radiation is constant. In order to provide an accurate measure of the illumination (as well as an accurate dose of radiation by the illuminator), the control circuit 24 compensates both for the temperature of the photodiodes in the radiometer during calibration and for the temperature of the photodiodes in the illuminator during viral inactivation. Electrical connecting wires (not shown) may pass through gaps 124, 126 between the shells 70, 71 and the box 118, providing electrical connections between the photo diodes 56, 68, amplifier circuits 128, 130, thermistors 136, 138 and the control unit 24. The wires pass as a cable through a block 140 (FIG. 5), comprised of two mating halves 142, 144, the lower half 142 of which is shown in FIG. 7 and FIG. 8. Spring plates 146, 148 may be provided adjacent the block on both the lower shell 70 and the upper shell 71, which may be engaged by a clamp (not shown) that holds a blood bag in position on the illuminator.

Each of the photo sensors 56, 68 is electrically coupled to transimpedance amplifiers 128, 130 respectively. The amplifiers 128, 130 are further electrically connected through a communications cable to the control unit 24. Male and female plugs (not shown) may be provided so that the radiometer may be selectively coupled to the control unit 24 for calibrating the apparatus, and then removed for ordinary operation. As shown in FIG. 11, the transimpedance amplifiers comprise an operational amplifier 100 receiving input from a photo sensor 102. The gain is controlled by both a manual variable resister 104 and a digital variable resister 106. The signal is then fed to a second operational amplifier 108 before being conducted to the control unit 24. It is anticipated that the variable resisters will be initially adjusted in comparison to a standardized light source, and would not need further adjustment when used in connection with a pathogen inactivation apparatus.

To calibrate a pathogen in activation apparatus, the radiometer 40 is substituted for a blood bag, and occupies the same location in the apparatus and has the same general shape as a blood bag containing blood or blood components. The radiometer would be electrically connected to the control unit 24 and exposed to radiation from the lamps 18, 30 for a selected period of time. Preferably, the platen 20 would also be agitated it the same manner as when a blood sample would be treated in the apparatus. The output of the radiometer provides a benchmark to the control unit 24 of exposure intensity per unit time, from which a desired dose of radiation can be calculated. After calibration of the apparatus, units of blood or blood components in appropriate translucent or transparent bags can be placed in the pathogen inactivation apparatus and exposed to controlled quantities of radiation.

Figure 9:
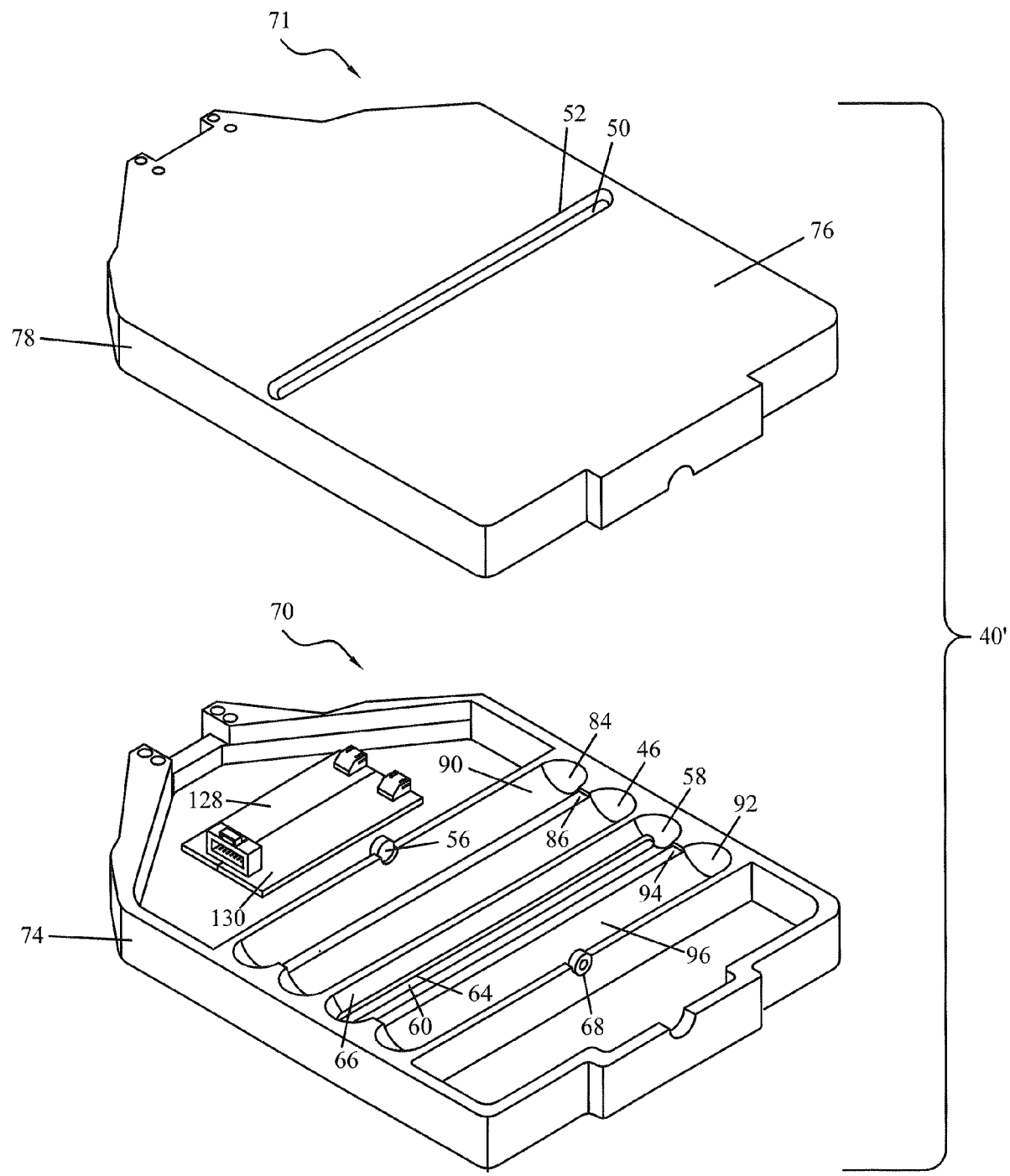
FIG. 9 is an exploded perspective view of a four-chamber radiometer.
Figure 10:
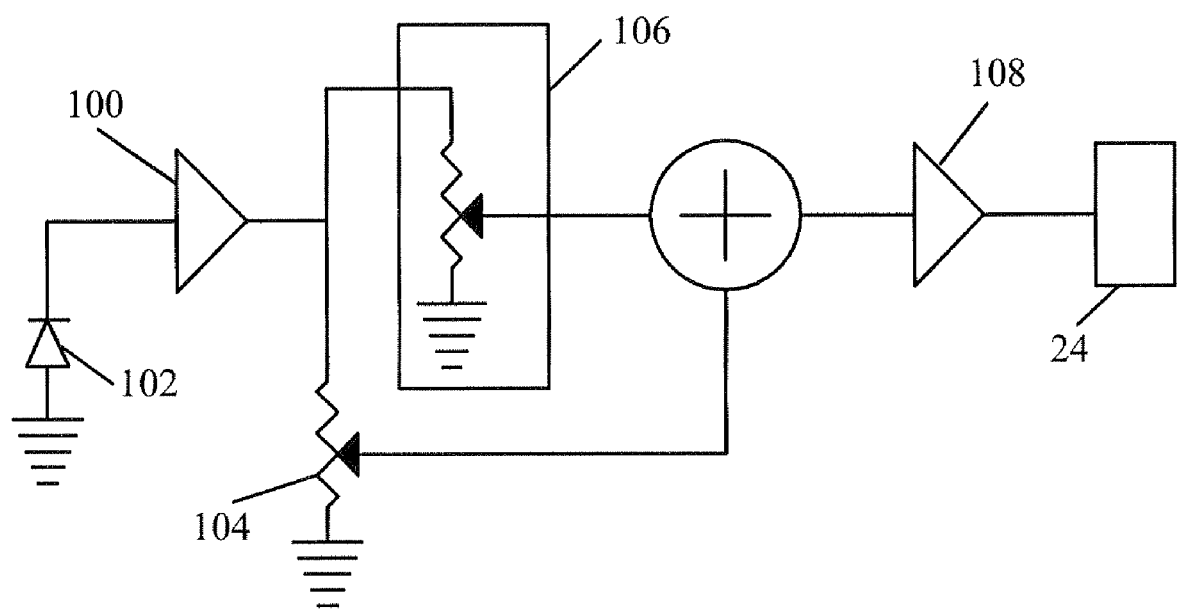
FIG. 10 is a schematic diagram of an amplifier for use in the radiometer.

Another embodiment of the radiometer 40' is shown in FIG. 9. In this embodiment, the first optical chamber 46 is connected to a first elongated, cylindrical integrating chamber 84 through a third slot 86. The walls of the first integrating chamber 84 are also optically rough and preferably made from TEFLON™ material or TEFLON-coated. In this embodiment, the photo sensor 56 is mounted in the inner wall 90 of the first integrating chamber, rather than in the inner wall of the first optical chamber.

Similarly, a second elongated, cylindrical integrating chamber 92 connects to the second optical chamber 58 through a fourth slot 94. As above, the photo sensor 68 is mounted in the inner wall 96 of the second integrating chamber 92, rather than in the inner surface 66 of the second optical chamber 58. The inner wall 96 is also optically rough and preferably made from TEFLON™ material or TEFLON-coated. The additional first and second integrating chambers 84, 92 further integrate the received illumination, providing a more representative measurement at the respective photo sensors, but at the cost of a decrease in absolute intensity.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. An irradiation apparatus for inactivating pathogens or white blood cells in a fluid containing blood components comprising:
   at least one radiation emitting source, said source emitting radiation suitable for inactivating pathogens or white blood cells in a fluid containing blood components; and
   a control unit for controlling the radiation emitting source,
   a radiometer in electrical communication with said control unit, said radiometer comprising
      a first elongated optical chamber having a first slot between said at least one radiation emitting source and said optical chamber, said first slot for receiving at least some of said radiation into said optical chamber and a photo sensor responsive to said received radiation in said optical chamber,
      a first elongated integrating chamber optically coupled to said first optical chamber by a second slot and wherein said sensor is in said first integrating chamber,
      wherein said second slot is generally perpendicular to said first slot with respect to an axis of symmetry of said first optical chamber.

2. The irradiation apparatus of claim 1 wherein said sensor is recessed away from an inner surface of said first integrating chamber.

3. The irradiation apparatus of claim 1 wherein said sensor is mounted diametrically across said first integrating chamber from said second slot.

4. An irradiation apparatus for inactivating pathogens or white blood cells in a fluid containing blood components comprising:
   at least one radiation emitting source, said source emitting radiation suitable for inactivating pathogens or white blood cells in a fluid containing blood components; and
   a control unit for controlling the radiation emitting source,
   a radiometer in electrical communication with said control unit, said radiometer comprising a first optical chamber having an aperture between said at least one radiation emitting source and said optical chamber, said aperture for receiving at least some of said radiation into said optical chamber and a photo sensor responsive to said received radiation in said optical chamber;
   a second radiation emitting source emitting radiation;
   said radiometer being mounted between said radiation emitting source and said second radiation emitting source, said radiometer further comprising a second optical chamber having a second aperture between said second radiation emitting source and said second optical chamber, said second aperture for receiving at least some of said radiation from said second radiation source and a second photo sensor responsive to said received radiation in said second optical chamber.

5. The irradiation apparatus of claim 4 wherein said optical chambers comprise parallel cylinders.

6. The irradiation apparatus of claim 5 wherein said first and second apertures comprise slots extending essentially parallel to a longitudinal axis of symmetry of the respective optical chamber of said slot.

7. The irradiation apparatus of claim 6 wherein said photo sensors are mounted in their respective chambers essentially perpendicularly to their respective slots with respect to their respective axis of symmetry.

8. The irradiation apparatus of claim 7 wherein said photo sensors are recessed away from an inner wall of their respective optical chambers.

9. The irradiation apparatus of claim 4 further comprising a first integrating chamber coupled to said first optical chamber by a first opening and a second integrating chamber coupled to said second optical chamber by a second opening and wherein said first sensor is in said first integrating chamber and said second sensor is in said second integrating chamber.

10. The irradiation apparatus of claim 9 wherein said optical chambers are parallel elongated cylinders having substantially parallel longitudinal axes of symmetry and wherein said apertures and said openings are slots, said slots being substantially parallel to said axes of symmetry.

11. The irradiation apparatus of claim 10 wherein said slots coupling said first and second integrating chambers to said first and second optical chambers are substantially perpendicular to said slots in said first and second optical chambers respectively with respect to said axes of symmetry of said first and second optical chambers respectively.

12. The irradiation apparatus of claim 11 wherein said first sensor is recessed away from an inner surface of said first integrating chamber and said second sensor is recessed away from an inner surface of said second integrating chamber.

13. The irradiation apparatus of claim 12 wherein said first sensor is mounted diametrically across said first integrating chamber from said slot in said first integrating chamber and said second sensor is mounted diametrically across said second integrating chamber from said slot in said second integrating chamber.

14. The irradiation apparatus of claim 4 wherein said radiometer further comprises a thermistor in thermal communication with said photo sensor and in electrical communication with said control unit, wherein said control unit is adapted to compensate for variations in the output of said photo sensor in response to an output of said thermistor.

15. The irradiation apparatus of claim 14, wherein a heat sink connects said photo sensor to said thermistor.

16. The irradiation apparatus of claim 4 wherein said irradiation apparatus further comprises at least one photo diode in optical communication with said radiation emitting source, and a thermistor in thermal communication with said photo sensor and in electrical communication with said control unit, wherein said control unit is adapted to compensate for variations in the output of said photo sensor in response to an output of said thermistor.

17. The irradiation apparatus of claim 16, wherein a heat sink connects said photo sensor to said thermistor.

* * * * *